(12) United States Patent
Schmitz et al.

(10) Patent No.: US 6,690,962 B2
(45) Date of Patent: Feb. 10, 2004

(54) PROCESS FOR GRAPHIC VISUALIZATION AND DIAGNOSIS OF THROMBI BY MEANS OF NUCLEAR SPIN TOMOGRAPHY WITH USE OF PARTICULATE CONTRAST MEDIA

(75) Inventors: Stephen Schmitz, Berlin (DE); Mayk Kresse, Berlin (DE); Susanne Wagner, Berlin (DE)

(73) Assignee: Institut fur Diagnostikforshung GmbH, Berlin (DE)

( * ) Notice: Subject to any disclaimer, the term of this patent is extended or adjusted under 35 U.S.C. 154(b) by 0 days.

(21) Appl. No.: 09/952,029

(22) Filed: Sep. 14, 2001

(65) Prior Publication Data

US 2002/0087071 A1 Jul. 4, 2002

Related U.S. Application Data

(60) Provisional application No. 60/235,553, filed on Sep. 27, 2000.

(51) Int. Cl.[7] .............................................. A61B 5/055
(52) U.S. Cl. ....................... 600/420; 600/407; 600/431
(58) Field of Search ................................ 600/420, 431, 600/407

(56) References Cited

U.S. PATENT DOCUMENTS

| | | | | |
|---|---|---|---|---|
| 5,190,744 A | * | 3/1993 | Rocklage et al. ........... | 324/306 |
| 5,260,050 A | * | 11/1993 | Ranney ....................... | 424/617 |
| 5,792,056 A | * | 8/1998 | Prince ........................ | 600/420 |
| 5,834,020 A | * | 11/1998 | Margerum et al. .......... | 424/484 |
| 6,048,515 A | * | 4/2000 | Kresse et al. ............. | 424/9.322 |
| 6,088,613 A | * | 7/2000 | Unger ........................ | 600/420 |

FOREIGN PATENT DOCUMENTS

| | | |
|---|---|---|
| DE | 19811349 C1 | 10/1999 |
| WO | WO 96/27394 | 9/1996 |
| WO | WO 00/72037 A4 | 5/2000 |
| WO | WO 00/61191 A2 | 10/2000 |

OTHER PUBLICATIONS

Schmitz et al. "SPIO–enhanced MR Angiography for the Detection of Venous Thrombi in an Animal Model," Rofo Fortschr Geb Rontgenstr Neuen Bildgeb Verfahr Mar;170(3):316–21 (1999).*

Schmitz et al. "USPIO–enhanced Direct MR Imaging of Thrombus: preclinical evaluation in rabbits," Radiology Oct:221(1):237–43 (2001).*

Small, W. et al., Dual Contrast Enhancement of Both T1–and T2–Weighted Sequences Using Ultrasmall Superparamagnetic Iron Oxide, Magnetic Resonance Imaging (11): 645–654 (1993).

* cited by examiner

Primary Examiner—George Manuel
Assistant Examiner—Barry Pass
(74) Attorney, Agent, or Firm—Millen, White, Zelano & Branigan, P.C.

(57) ABSTRACT

The invention relates to a new process for graphic visualization and diagnosis of thrombi as well as the use of particle suspensions for the production of contrast media for the visualization of thrombi with use of nuclear spin tomography.

6 Claims, 8 Drawing Sheets

[Key:]

Lange des Thrombus n der Röntgen-Phlebography = Length of the Thrombus n of Radiologic Phlebography Kontrollen = Controls Zeit nach Thrombusinduktion (TAGE) = Time After Thrombus Induction (DAYS)

[Key:]

Übereinstimmung der Thrombuslänge in der 3[ill.]-MPR mit der Rö-Phlbogra = Correspondence of the Thrombus Length in the 3[ill.]-MPR with the Radiologic Phlebography Ausgangs-MRT = Initial MRT Verlaufs-MRT = Plot MRT Gruppen = Groups

[Key:]

Thrombusstruktur in der T2*-gewiechteten Gradientenechosequenz =
    Thrombus Structure in the T2*-Weighted Gradient Echo
    Sequence heterogen-konzentrisch = Heterogeneous-concentric heterogen-ungeordnet = Heterogeneous-random homogen = Homogeneous Gruppen = Groups

[Key:]

Thrombussignal in der T2*-gewichteten Gradientenechosequenz = Thrombus Signal in the T2*-Weighted Gradient Echo Sequence Ausgangs-MRT = Initial MRT Verlaufs-MRT = Plot MRT Gruppen getrennt nach Thrombusalter (Tage) = Groups Separated According to Age of Thrombus (Days)

[Key:]

Kontrastumfang des Thrombus in der T2*-gewichteten
   Gradientenechosequenz = Extent of Contrast of the Thrombus
   in the T2*-Weighted Gradient Echo Sequence Ausgangsuntersuchung = Initial Study Verlaufsuntersuchung = Plot Study Gruppen getrennt nach Thrombusalter (Tage) = Groups Separated
   According to Age of Thrombus (Days)

PROCESS FOR GRAPHIC VISUALIZATION AND DIAGNOSIS OF THROMBI BY MEANS OF NUCLEAR SPIN TOMOGRAPHY WITH USE OF PARTICULATE CONTRAST MEDIA

This application claims the benefit of the filing date of U.S. Provisional Application Serial No. 60/235,553 filed Sep. 27, 2000.

The invention relates to a new process for graphic visualization and diagnosis of thrombi as well as the use of particle suspensions for the production of contrast media for the visualization of thrombi by means of nuclear spin tomography.

A thrombus is a circumscribed blood solidification that forms in arteries or veins by intravascular clotting. A thrombosis, i.e., a partial or complete obstruction of arteries or veins by a thrombus, can result in anemia and tissue death of an organ (infarction). A typical example of an arterial thrombosis is that of the coronary arteries (coronary thrombosis). If a thrombus detaches from the vessel wall, it is borne away by the blood stream. In terms of a thromboembolism, this thrombus can obstruct a downstream smaller vessel. The brain-supplying arteries are a typical example of thromboembolisms in arteries. The very common thromboses of the pelvic veins and leg veins typically result in a thromboembolism of the lung arteries. The lung artery embolism is especially feared since it is difficult to detect and often leads to a fatal outcome.

Thrombi are currently diagnosed with the aid of various processes. The most frequently used processes are catheter-radiologic angiography, radiologic phlebography and various ultrasound processes.

Angiography is increasingly performed with the aid of nuclear spin tomography (nuclear spin angiography), whereby the blood flow into the vessels is visualized. An example of this process is described by Siewert et al, Fortschr. Röntgenstr. 156 (1992), pp. 549–554. This process visualizes thrombi as areas with deficient flow into the vessel. Possible errors arise in smaller veins with slow or deficient flow. Such vessels are not visualized. The nuclear spin angiography with use of contrast media is an improvement relative to flow-dependent processes. An example of such a process is described by Schmitz et al. in Fortschr. Röntgenstr. 170 (1999), pp. 316–321. Intravenously-injected contrast media are mixed with the blood and selectively visualize those vessels in which the contrast medium-mixed blood is dispersed. Thrombi are indirectly visible as recesses (filling defects) in the vessels.

Not all vessels are reached in the case of radiologic phlebography. Of the ultrasound processes, that of the duplex-sonography FKDS, which, however, can visualize only surface veins and is ineffective in the pelvic area, is a frequently used process. All of these diagnostic processes provide results that are ambiguous and can result in misdiagnoses.

In International Patent Application WO 98/16256, a process for visualizing thrombi by means of nuclear spin tomography is proposed, in which contrast media that consist of chelating agents and integrin-binding molecules coupled thereto are administered to the patient. The chelating agents complex paramagnetic metal ions, such as, e.g., gadolinium ions.

Similar contrast media are also proposed in International Application WO 95/20603. The agents that are described there are peptides, to which one complexing agent in each case is coupled. The complexing agent can complex a metal ion, which can either release radioactive radiation and can be detected with a gamma camera or is a gadolinium ion or other paramagnetic metal ion that is suitable for use as a contrast medium in nuclear spin tomography.

These patent applications, however, describe only the synthesis of contrast media and first in-vitro tests. No in-vivo experiments or nuclear spin tomograms, with which the action of the agents could be demonstrated unambiguously, are shown. To date, such contrast media also have not been developed by pharmaceutical companies or cannot be purchased as usable contrast media.

There is therefore a need for new, unambiguous and reliable diagnostic processes for arterial and venous thrombi and for contrast media that are suitable for such a process.

The object of this invention is therefore to develop a new process for the diagnosis of arterial and venous thrombi and to find suitable contrast media for such a process.

This object is achieved with the new process according to claim 1 and the use of particle suspensions for the production of contrast media according to claim 6.

It was found, surprisingly enough, that MR blood pool-contrast media, such as superparamagnetic iron oxide (SPIO), especially in a formulation with small particles (ultrasmall superparamagnetic iron oxide, USPIO), accumulate in an animal model in experimental thrombi and are visible after a time interval of several blood half-lives in nuclear spin tomograms and can be used diagnostically. It was found that the contrast medium preferably accumulates in the thrombi but also frequently in the adjoining vessel wall and surrounding area.

In the process according to the invention, first a particulate MR-contrast medium is accordingly administered to the patient, and a nuclear spin tomogram is recorded after the contrast medium accumulates in the thrombus and/or the adjoining vessel wall and surrounding area (i.e., after a time interval of several blood half-lives). An especially good visualization is achieved with T1-weighted nuclear spin tomograms. After an intracellular recording of the contrast medium in the macrophages (phagocytes) of thrombi, an effect can also be produced in T2-weighted images.

The ultrasmall superparamagnetic iron oxide particles (USPIO) that are used in the experiment that is described in more detail below consist of an iron oxide nucleus and a carboxydextran shell. The mean diameter of the particles is preferably less than 50 nm, especially preferably approximately 25 nm. The production of such particles is described in, e.g., Patents EP 656 368 and WO 98/05430. A contrast medium that contains such particles is at present being developed by the Schering AG Company.

The iron-containing contrast media are used at, for example, a dosage of 200 $\mu$mol of Fe/kg of body weight.

After a waiting time of several blood half-lives, in which the contrast medium accumulates in the thrombi, images are recorded with a nuclear spin tomograph. The thrombi are clearly visible in the images that are obtained in such a way.

If the contrast medium accumulates extracellularly, then its T1-effect can make the thrombus visible by producing a strong signal in T1-weighted images. If the contrast medium of macrophages (phagocytes), which within the limits of thrombus degradation (thrombus organization) regularly migrate into the vessel wall or the edge of the thrombus, is recorded, the T2-effect of the contrast medium can predominate, by which the labeled tissue appears to produce little or no signal in T2- or T2*-weighted images.

Below, an animal experiment is described in detail, in which thrombi were produced in 25 rabbits by catheter embolization and thrombin injection into the external jugular vein. After 1, 3, 5, 7 and 9 days (each n=5), measurements were taken using T1w-MP-RAGE and T2*w-FLASH nuclear spin tomograms at 1.5 Tesla before and 24 hours after intravenous administration of ultrasmall superparamagnetic iron oxide (USPIO, particle size about 25 nm) at a dose of 200 μmol of Fe/kg of body weight. The radiologic phlebography and histology were used as a gold standard. The length of the thrombus visible in 3D-reconstructions of the T1w-MP-RAGE sequence was expressed in a ratio to true thrombus length. The structure, the signal intensity and the extent of contrast of the thrombus in the T2*w-technology were subjected to a subjective analysis with a defined scaling. 25 rabbits with age-appropriate thrombi were used as controls.

This experiment is to illustrate the invention without intending to be limited to this experiment.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure[s] of all applications, patents and publications, cited above [or below], and of corresponding German application No. DE 100 46 514.5, filed Sep. 15, 2000, and U.S. Provisional Application Serial No. 60/235,553, filed Sep. 27, 2000, are hereby incorporated by reference.

Example of the Detection of Experimental Thrombi by Means of Nuclear Spin Tomography after Injection of Particulate Contrast Media Material and Method Contrast Media A formulation of ultrasmall superparamagnetic iron oxide particles (USPIO) was used. The particles consist of an iron oxide nucleus and a carboxydextran shell with a total diameter of 25 nm. In the rat, the effective plasma half-life is 56±17 minutes, and the LD50 is 35 mmol of Fe/kg of body weight. In the rabbit, the estimated plasma half-life is about 6 hours. The contrast medium was injected slowly at a dosage of 200 μmol of Fe/kg of body weight in a volume of 2–3 ml into an ear vein of the healthy side, followed by 2 ml of physiological common salt solution.

Animal Model

The experiments were performed in accordance with the German law for the Protection of Animals. The responsible national authority has given permission. Chinchilla bastard rabbits of both sexes (2.6–3.8 kg) were used. All studies were performed in low anesthesia by subcutaneous injection of 40 mg/kg of ketamine-HCl (ketanest-50, Parke-Davis GmbH, Berlin) and 17 mg/kg of xylazine-HCl (Rompun 2%, Bayer, Leverkusen). Before the thrombus induction, the neck veins were first documented in two planes by using radiologic phlebography with injection of a standard contrast medium into an ear vein. In a way similar to the method used by Wessler, a thrombostasis was produced by blood stasis and hypercoagulability [Wessler S. Thrombosis in the Presence of Vascular Stasis. Am J Med 1962; 33:648–666.] The stasis was not created by operative ligature of the veins, but rather by a catheter embolization. From an ear vein, an approximately 20 cm long guide catheter (3 French) was advanced into the external jugular vein with the aid of a sluice and a guide wire. Using the guide catheter, a microcatheter with an outside diameter of 0.61 millimeters was positioned with the tip of the catheter at the level of the 4th or 5th cervical vertebra. The embolizate, a mixture of an oily, iodine-containing lymphographic x-ray contrast medium (lipiodol, Byk Gulden, constancy) and a butylcyanoacrylate-tissue adhesive (histoacryl, B. Braun, Melsungen) at a 1:1 ratio, was injected slowly in such a way that, on the one hand, the embolizate could adhere to the vessel wall and, on the other hand, a mixing of embolizate and blood could be carried out. After the vessel was closed, 100 units of bovine thrombin (Sigma-Aldrich, Chemie GmbH, Steinheim) was administered via a second microcatheter. The embolizate should lead to a passage-like closure of the vessel for a few days. The embolizate should be both x-ray-opaque to the radiological phlebography because of the proportion of iodine, and be visible in a hyperintense manner because of the T1-weighted MRT-images in the adhesive-fixed blood degradation products.

Experimental Design

Fifty thrombus-carrying test animals were randomly assigned to contrast medium group (D) or to control group (K). A related breaking down took place according to thrombus age at the time of the first MRT measurement (1, 3, 5, 7 or 9 days). Consequently, an assignment was made respectively in 5 contrast medium groups (D1, D3, D5, D7 and D9) and 5 control groups (K1, K3, K5, K7 and K9). Each subgroup comprised five test animals. In all the test animals, the thrombus was documented via radiologic phlebography before the initial MRT. After this initial MRT, animals of contrast medium group (K) received the contrast medium, and after a 24-hour interval, they received the plot-MRT. In group D3, e.g., after embolization on day 0, an initial MRT took place on day 3, and a plot-MRT took place on day 4. Of the controls, only animals of groups K1, K3 and K5 received a plot-MRT, but not animals of groups K7 and K9, which had been measured at the beginning of the experiment, as the length of the plot interval was not fixed.

MRT

The studies were performed in a 1,5-tesla magnet (vision, Siemens, Erlangen) with a standard knee-coil. The anesthetized animals were positioned in dorsal recumbent position in a U-shaped foam base. A water-containing plastic bag was placed on the ventral neck side to enhance the fat saturation. T1-weighted images were produced in coronary layer orientation with a 3D-magnetization-prepared rapid gradient-echo imaging-sequence (3-DMP-RAGE) [Mugler, JPd, Brookeman, J. R. Three-dimensional Magnetization-Prepared Rapid Gradient-Echo Imaging (3D MP RAGE). Magn Reson Med 1990; 15:152–7.]. The sequence that is used suppresses the signal from fat by a sequence-inherent selective water excitation pulse and that of blood by the selection of the delay time [Moody, A. R.; Pollock, J. G.; O'Connor, A. R.; Bagnall, M. Lower-limb Deep Venous Thrombosis: Direct MR Imaging of the Thrombus. Radiology 1998; 209: 349–55.]. The following parameters were used: repetition time 10.3 ms; echo time 4.0 ms; 15° flip angle; inversion time 20 ms; delay time 1.000 ms; number of layers 100; acquisitions 1; layer thickness 0.8 mm; image field 100×200 mm; matrix 128×256; acquisition time 5:30 minutes; pixel size 0.78×0.78×0.8 mm. Of the 2D-source images, about 1.5 cm thickness 3D-maximum-intensity-projection reconstructions (MIP) were produced.

T2*-weighted axial images were produced with a 3D-gradient echo sequence (Fast Low Angle Shot, FLASH) [Frahm, J.; Haase, A.; Matthaei, D. Rapid Three-dimensional MR Imaging Using the FLASH Technique. J Comput Assist Tomogr 1986; 10:363–8]. The sequence visualizes the vein lumen in a hyperintense manner in fat and muscles by using the sequence-inherent bright-blood effect. By the moderate T2*-weighting, intracellularly accumulated blood degradation products or SPIOs are to be imaged with little or no signal. The following imaging parameters were used: repetition time 54 ms; echo time 18 ms; 15° flip angle; block density thickness 80 mm, partitions 40; layer thickness 2 mm; image cutaway 80×80 mm; matrix 256×256; acquisition time 22:08 minutes; pixel size 0.31×0.31×0.2 mm.

Pathology

According to the plot-MRT, the animals were sacrificed by an overdose of xylazine. The caudal and cranial segments of the external jugular vein and the common facial vein were prepared, set in 10-percent formalin for 24 hours and split up into five vascular cylinders apiece, 3 mm in length. After being embedded in paraffin, the caudal end of each cylinder was cut to a thickness of 3 $\mu$m and dyed with Berliner blue on iron.

Image Analysis

The histological sections, hard-copies of the phlebographies and the MRTs were evaluated by a radiologist. The length of the thrombus in the external jugular vein was measured with the aid of phlebography. The histology was used as a second detection process of the thrombus, especially in the case of fresh, occlusive thrombi that were not flushed with contrast media. Because of the well-known shrinking artifacts during the histological working-up, however, it is suitably only limited to length determinations.

Then, the length of the thrombus was determined with the T1-weighted 3D-reconstructions of the MP-RAGE sequence. The thrombus was defined as visible if it could be delineated from the surrounding area in a hyperintense and clear manner. In an incomplete visualization, only the visible thrombus portions were measured. To eliminate an influence of the individual and thrombus-age-dependent variance of the thrombus length, the thrombus length determined by the gold standard was standardized to 1.0, and the thrombus length measured in the 3D-reconstruction of the MP-RAGE sequence was indicated in portions of 1.0, e.g., 0.4.

The T2*-weighted gradient echo sequence images were subjected only to a qualitative analysis. For the evaluation, a representative layer was selected, which was clearly detected by the reference methods and was characteristic of the individual thrombus. In the case where it was not possible to delimit the thrombus clearly from the surrounding blood, it was possible to use the reference method to locate the thrombus. The structure of the thrombus was classified as "homogeneous," "heterogeneousrandom" or "heterogeneous-concentric" (central hyperintense, peripheral hypointense). The signal intensity of the "homogeneous" thrombus, the leading signal intensity, i.e., the largest visible thrombus portion of the "heterogeneous-random" thrombus or the signal intensity of the center in the case of a "heterogeneous-concentric" thrombus was graded from no signal to strong signal on a 5-point scale:

1.—No signal, signal intensity such as compact bone or background
2.—Little or no signal, between 1 and 3
3.—Moderate signal intensity, muscle-isointense
4.—Strong signal, between 3 and 5
5.—Very strong signal, corresponding to a "light bulb effect"

The extent of contrast of the thrombus was determined as the difference between the minimum and maximum signal intensity based on the definitions of the signal intensity. This is based on a 4-point scale.

To study a contrast medium concentration of the wall and surrounding vascular area in the thrombus-carrying veins, the surrounding area was graded from muscle-isointense (normal) or little or no signal in a representative layer of the T2*-weighted sequence.

Statistics

The data were combined with the mean value and the standard deviation broken down by groups (controls, contrast media) and the thrombus age (days) or graphically visualized (Stat View 4.5, SAS Institute Inc., Cary, N.C., USA). A comparison of the first measurement with the plot measurement was carried out with the t-test for pair comparisons respectively broken down for groups D and K. The individual groups, e.g., D1 versus K1, were compared to the variance analysis (ANOVA), for which significance testing was performed with the Fischer Test (Fischer's Protected Least Significant Difference, PLSD). The significance level in all cases was $p<0.05$.

Results

Animal Model

Seven animals died during or after the catheter embolization by a shock reaction presumably by mechanical stimulation of blood pressure regulators, by bearing away the embolizate into the lungs or for unexplained reasons. These animals were excluded from the experiment. In the other animals, it was possible to produce thrombi in all cases. Based on the lipiodol portion, the embolizate could be detected in all cases in the radiologic phlebography (FIGS. 1 and 2). In 44 of the 50 cases, it was also visible with a strong signal in the 3D-MIP-reconstruction of the MP-RAGE-sequence. In the other six cases, it was possible to discern the MP-RAGE-sequence at least in the 2D-source images.

By radiologic phlebography, the length of the thrombus in the external jugular vein of group K1 of the control was 43±8 and in group D1 of the contrast medium animals, it was 36±10 mm. The length clearly decreased in the testing period and was 23±10 or 11±8 mm in groups K9 m and D9 (FIG. 3). A significantly different length between control and contrast medium groups of the same thrombus age did not exist at any point in time.

Histologically found in groups K1 and D1 was a fresh thrombus that consists of tightly packed erythrocytes (hemostasis) permeated with fibrin trabecula; in groups K3 and D3 a tightly packed hemostasis with central resolution of the erythrocytes in individual animals; in groups K5 and D5 a resolution of erythrocytes in the center of the thrombus in all cases (homogenization) as well as the marginal migration of mononuclear cells; in groups K7 and D7 the increasing permeation of the thrombus by mononuclear cells and the incipient endothelialization with isolated crossing capillaries; and in groups K9 and D9 the almost complete permeation of the thrombus by mononuclear cells and capillaries with an incipient connective tissue formation.

MRT

Thrombi were visible in the 3D-reconstructions of the T1-weighted MP-RAGE sequence as worm-shaped hyperintense structures (FIGS. 1 and 2). In the case of contrast medium animals, a slightly increased signal in the larger neck vessels in terms of a residual angiography effect was found in the plot measurement. Without taking into consideration the age of the thrombus, in group K an agreement of the relative thrombus length of the 3-DMP-RAGE sequence of the initial-MRT and phlebography of 0.2±0.3 was found, and in D, 0.1±0.3. In the animals of group D (n=25), a significant increase of the corresponding relative thrombus length of 0.1±0.3 was found in the 24-hour plot before the contrast medium was raised to 0.5±0.5 for 24 hours, p=0.001 (FIGS. 1, 2 and 4); but not in the case of controls (only groups K1, K3 and K5), p=0.34. The analysis of the individual daily groups shows a dependence of the thrombus portion visible in the MP-RAGE sequence on the thrombus age (FIG. 4). This was 0.2±0.3 to 0.4±0.5 in the low thrombus age in groups K1, K3 and K5, or 0.1±0.1 and 0 in the higher age in groups K7 and K9. After the administration of contrast medium, a significant increase of the visible thrombus portion was shown in the following groups: D3, from 0.6±4 to 0.8±0.4; D5, from 0.1±0.1 to 1±0.1; and D7, from 0 to 0.6±0.4. No significant difference was found in the contrast medium animals of groups D1 and D9.

The moderate T2*-weighted FLASH-sequence showed a considerable thrombus-age-dependent variability of the structure, the signal intensity and the extent of the contrast. An individual example is found in FIG. 5. In the controls, the "heterogeneous-random" and "heterogeneous-concentric" thrombus structure was weighed up to the 7th day (FIG. 6). Starting from the 7th day, a "homogeneous" thrombus structure predominates in the controls. In control animals K1, the leading signal intensity of the thrombus was the "moderate," i.e., isointense in the muscles, but with a clear scattering (FIG. 7). Up to the 3rd day, the signal intensity of the thrombus increased in the control animals tending toward "strong signal" to decrease up to the 9th day to an intensity defined as having "little or no signal." The extent of the contrast of fresh thrombi was on average 1.6 in group K1 and 0.4 in group K9 (FIG. 8). Ultimately, only in four animals of group K after contrast medium was administered was a signal reduction of the thrombus found in the moderate T2*-weighted FLASH sequence, which was evaluated as a possible contrast medium effect (FIG. 5). A comparison to the starting measurement and the plot measurement in totality or broken down by thrombus age indicated no significant change of the thrombus structure (FIG. 6), the thrombus signal (FIG. 7) or the extent of contrast of the thrombus (FIG. 8).

In 6 of 50 animals, under already native conditions, a partial signal attenuation (n=4) or circular signal attenuation (n=2) of the wall and the immediately surrounding vascular area was found in representative layers of the T2*-weighted sequence. After the administration of contrast medium, the lack of signal existed in all 6 animals. In 11 other animals, a lack of signals of the wall and immediately surrounding vascular area was found only in the plot control, in 2 animals in the circular manifestation and in 9 animals in the partial manifestation. Of these 11 animals, one was a control. The other 10 had received contrast media. Of these 10 contrast-enhanced studies, 4 were from group D1 and 4 from D3, i.e., the contrast medium concentration of the vein wall and immediately surrounding vascular area were preferably found in young thrombus stages in 4 out of every 5 cases.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

Figure 1:
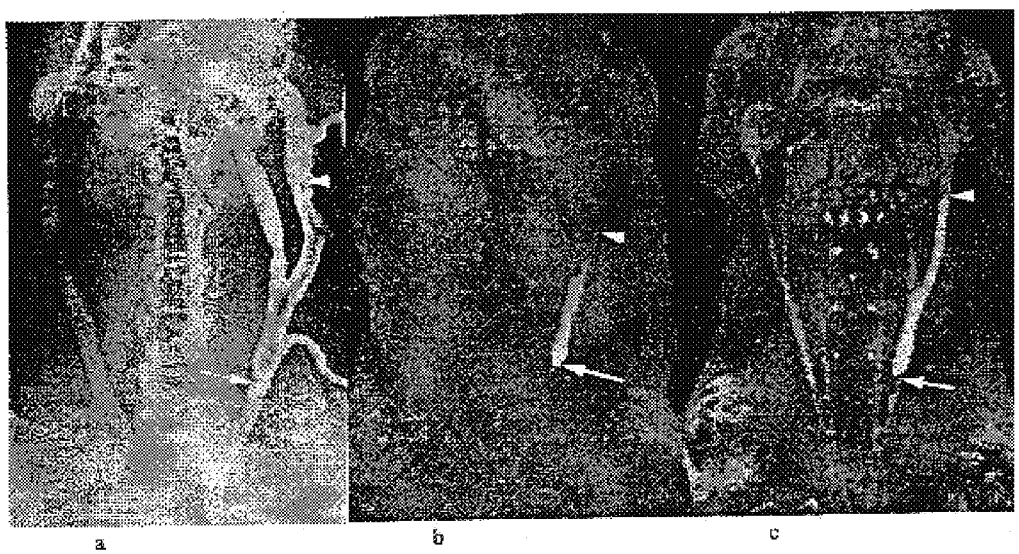
FIG. 1
Figure 2:
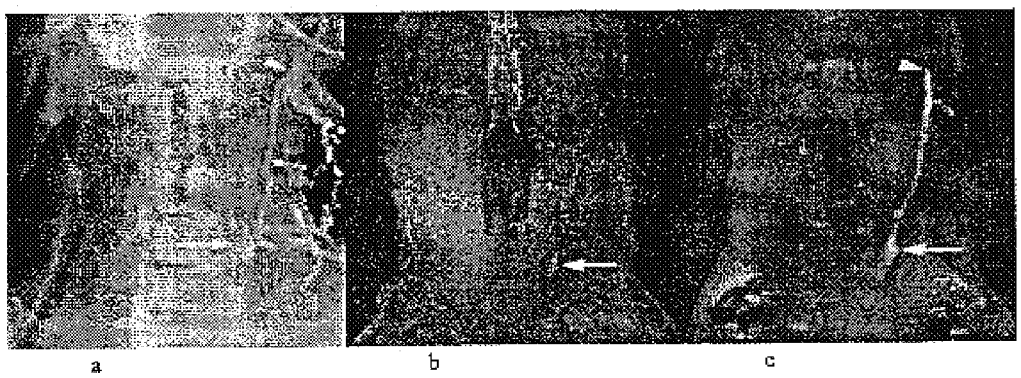
Figure 3:
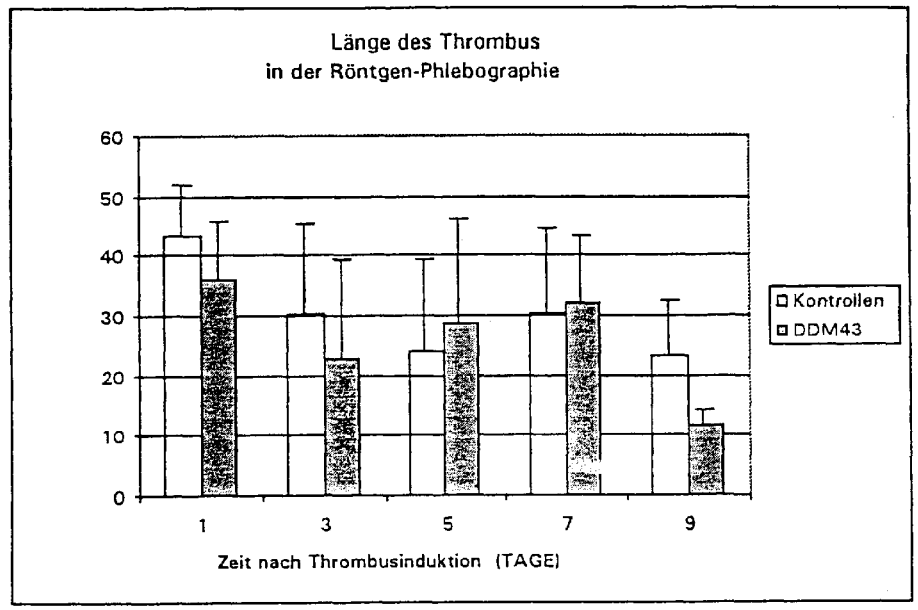
Figure 4:
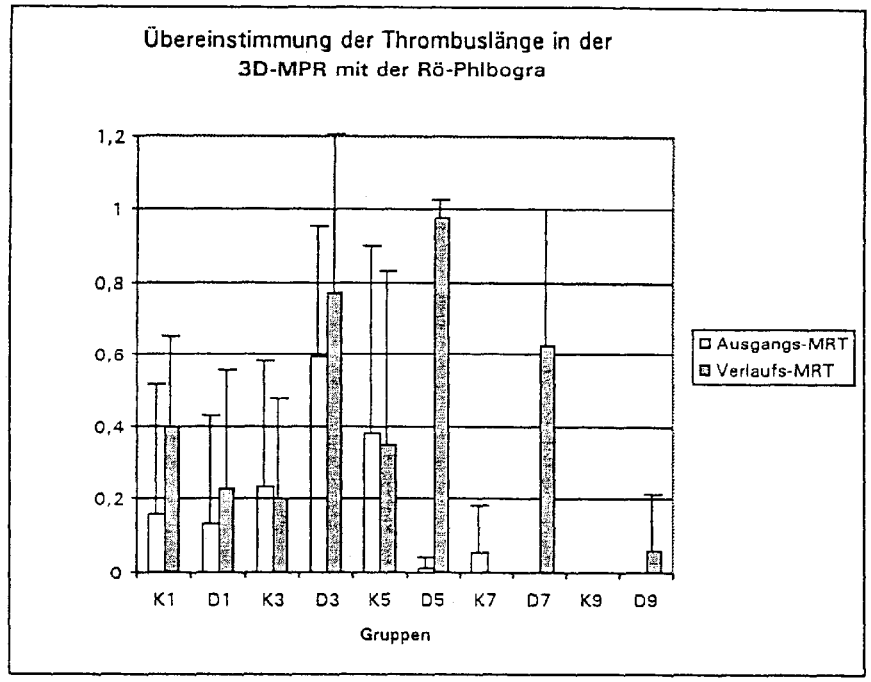
Figure 5:
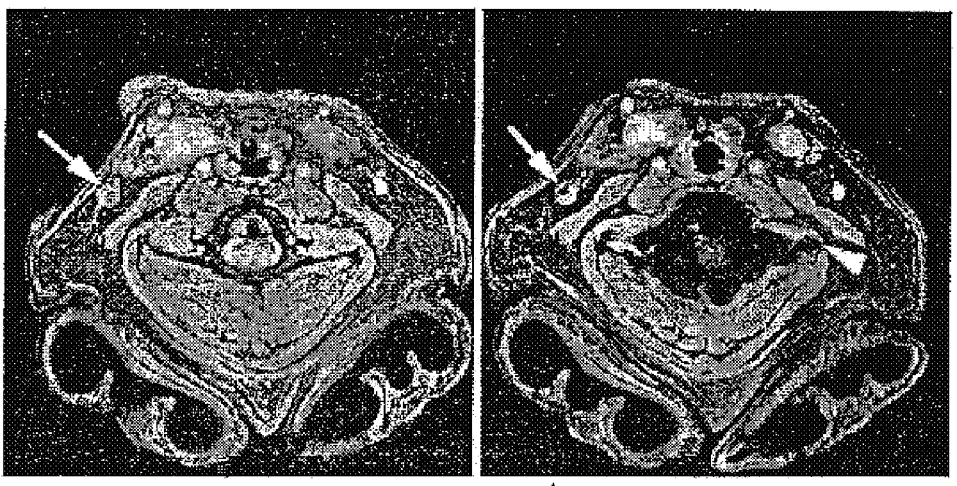
Figure 6:
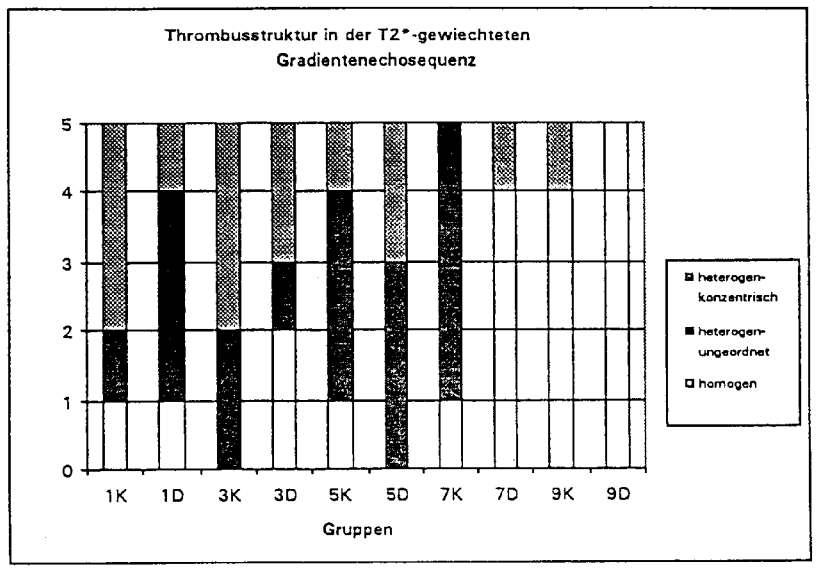

Radiologic phlebography (a) shows an incomplete closure of the left external jugular vein three days after thrombus induction. The external jugular vein receives a further intake from the middle cardiac vein, the common facial vein. The outflow of the contrast medium is carried out in some cases via the opposite side. The embolizate (arrow) is x-ray-opaque in phlebography (a). In 3D-reconstructions of the MP-RAGE-sequence, the position of the embolizate before (b) and 24 hours after the administration of superparamagnetic iron oxide (c) is labeled by an arrow. The cranial end of the visible thrombus portion was labeled in each case by an arrowhead (b and c). After contrast medium was administered (c), additional cranial thrombus portions are visible in the MP-RAGE-sequence in comparison to the initial MRT (b). After contrast medium was administered, a complete correspondence of the thrombus length was present in the MP-RAGE-sequence and the gold standard. A residual angiography effect of the contrast medium is also found in other neck vessels.

FIG. 2

Five days after embolization, an embolizate (arrow) can be detected in radiologic phlebography (a). Individual thrombus portions are flushed in the cranial internal jugular vein (a, arrowhead). Ipsilateral collaterals are found (a, thinner arrow). In the 3D-reconstruction of the native MP-RAGE-sequence, the thrombus cannot be detected and the embolizate is hard to detect (b, arrow). 24 hours after the administration of contrast medium (c), the entire thrombus is visible from the embolizate (arrow) to the cranial external jugular vein (arrowhead) and a lateral ear vein.

FIG. 3

Length of the thrombus in the external jugular vein. A reduction in the thrombus length from day 1 to 9 is shown.

FIG. 4

Agreement of the relative thrombus length in 3D-reconstruction of the T1-weighted MP-RAGE-sequence and radiologic phlebography broken down by contrast medium animals (D) and controls (K) as well as thrombus age (1–9 days). The result of the initial MRT and the 24-hour-plot-MRT is shown. Deficient agreement is expressed by the value 0, complete agreement by 1. After DDM34 is administered, a significantly higher correspondence of the thrombus length that is visible in the MPR-RAGE-sequence was found in groups D3, D5 and D7, but not in fresh thrombi (D1) and organized thrombi (D9).

FIG. 5

In the moderate T2*-weighted FLASH-sequence, a seven-day-old thrombus with a thrombus structure defined as "homogeneous" and a "moderate" signal intensity is found in the external jugular vein (arrow) before the administration of contrast medium (a). After the contrast medium is administered, the thrombus has "little or no signal" (b, arrow). Significant signal loss of the fluidized column after administration of SPIO (b, arrowhead).

FIG. 6

Thrombus structure in the T2*-weighted FLASH-sequence in controls (K) and animals before the administration of contrast medium (D) broken down by days (1st–9th day). Up until the 7th day, the heterogeneous thrombus structure is predominantly heterogeneous-random and heterogeneous-concentric. Starting from about the 7th day, the homogenous thrombus structure predominates.

Figure 7:
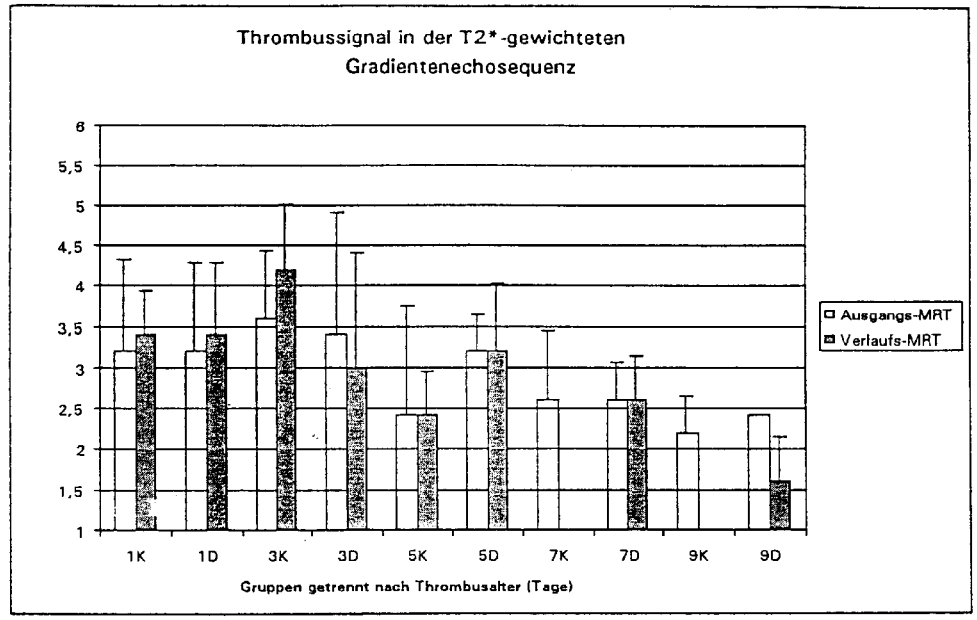
Figure 8:
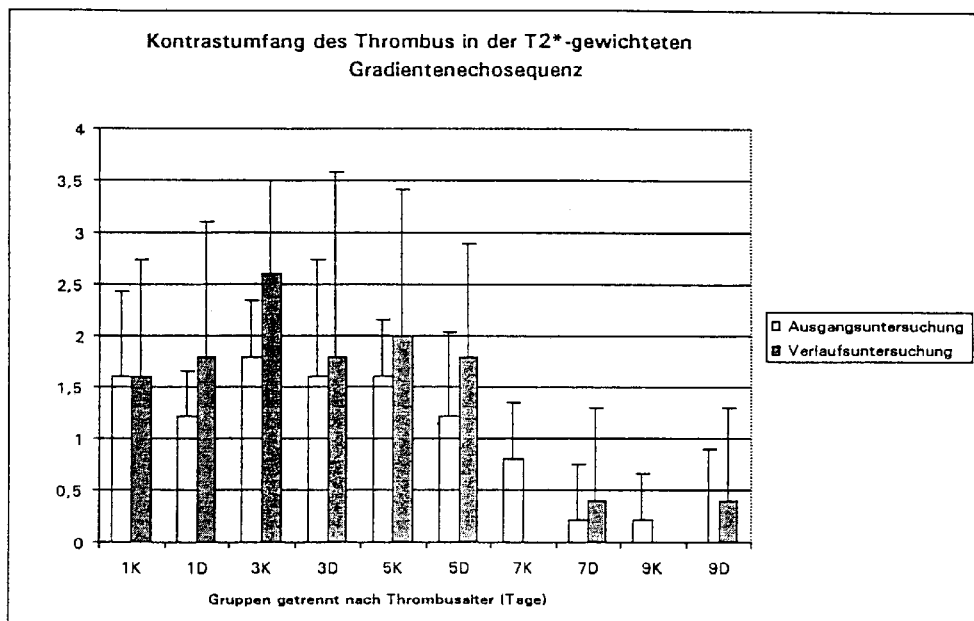

FIG. 7 Signal intensity of the thrombus in the T2*-weighted FLASH-sequence on a 5-point scale of no signal (1), little or no signal (2), muscle-isointense (3), strong signal (4) and very strong signal (5). Groups of controls (K) and contrast medium animals are visualized broken down by thrombus age. Both the initial MRT and the plot-MRT are shown—there is no plot-MRT in the controls of K7 and K9.

FIG. 8

Extent of contrast of experimental thrombi in the T2*-weighted gradient sequence. It is shown that the extent of contrast both in controls (K) and in contrast medium animals (D) decreases over a period of nine days, i.e., the thrombus is homogeneous. A significant change of the extent of contrast between the initial study and the plot study is not found in any group.

What is claimed is:

1. A method for graphic visualization and/or diagnosis of a thrombus, comprising administering a particulate MR-contrast medium to a patient, and after a sufficient amount of contrast medium has accumulated in the thrombus and/or the adjoining vessel wall and surrounding area to enhance an MR image thereof, taking a nuclear spin tomogram of the thrombus and/or the adjoining vessel wall and surrounding area, wherein the particulate contrast medium contains ultrasmall superparamagnetic iron oxide particles having a mean particle diameter of less than 50 nm.

2. A method according to claim 1, wherein the nuclear spin tomogram is taken as a Ti-weighted image.

3. A method according to claim 1, wherein the nuclear spin tomogram is taken as a T2- or T2* -weighted image.

4. A method according to claim 1, wherein the particulate contrast medium contains superparamagnetic iron oxide particles having a mean particle diameter of about 25 nm.

5. A method according to claim 1, wherein 200 $\mu$mol of contrast medium is administered to the patient.

6. A method according to claim 1, wherein the nuclear spin tomogram is taken about 24 hours after the administration of the contrast medium.

* * * * *